US009360419B2

(12) United States Patent
Molter et al.

(10) Patent No.: US 9,360,419 B2
(45) Date of Patent: Jun. 7, 2016

(54) METHOD OF SPECTROMETRY AND SPECTROMETER

(71) Applicant: HÜBNER GmbH & Co. KG, Kassel (DE)

(72) Inventors: Daniel Molter, Kaiserslautern (DE); Frank Ellrich, Fürfeld (DE); Daniel Hübsch, Kassel (DE); Thorsten Sprenger, Lohfelden (DE)

(73) Assignee: HÜBNER GmbH & Co. KG, Kassel (DE)

( * ) Notice: Subject to any disclaimer, the term of this patent is extended or adjusted under 35 U.S.C. 154(b) by 6 days.

(21) Appl. No.: 14/608,539

(22) Filed: Jan. 29, 2015

(65) Prior Publication Data

US 2015/0369729 A1  Dec. 24, 2015

(30) Foreign Application Priority Data

Feb. 3, 2014  (DE) .......................... 10 2014 101 302

(51) Int. Cl.
*G01N 21/3581* (2014.01)
*G01N 22/00* (2006.01)
(Continued)

(52) U.S. Cl.
CPC .............. *G01N 21/3581* (2013.01); *G01J 3/108* (2013.01); *G01N 21/3586* (2013.01); *G01N 22/00* (2013.01); *G01N 2201/06113* (2013.01); *G01N 2201/12* (2013.01)

(58) Field of Classification Search
CPC .............................. G01N 21/3581; G01J 3/108
See application file for complete search history.

(56) References Cited

U.S. PATENT DOCUMENTS

| 6,188,471 B1 | 2/2001 | Jung et al. |
| 6,690,817 B1 | 2/2004 | Cabib et al. |
| 7,463,345 B2 | 12/2008 | Cohen et al. |

(Continued)

FOREIGN PATENT DOCUMENTS

| EP | 0 727 671 A2 | 8/1996 |
| EP | 1 607 736 A1 | 12/2005 |

OTHER PUBLICATIONS

Extended European Search report issued Jun. 12, 2015 in corresponding European patent application No. 15 153 630.7 (6 pages).
(Continued)

*Primary Examiner* — David Porta
*Assistant Examiner* — Faye Boosalis
(74) *Attorney, Agent, or Firm* — Drinker Biddle & Reath LLP

(57) ABSTRACT

A method of spectrometry on a spatially extensive sample with generation of a measure in respect of a match of a detected spectrum of a first generation with a single or a plurality of predetermined comparative spectra of chemical substances is disclosed. The method includes the steps: determining at least one location of the first generation on the sample, irradiating the sample with electromagnetic radiation with a plurality of frequencies or a frequency band between 1 GHz and 30 THz at the given location of the first generation of a first order on the sample, frequency-resolved detection of a measure in respect of the intensity of the electromagnetic radiation irradiated on to the sample at the location of the first generation and transmitted or reflected by the sample as the spectrum of the first generation, and calculating a respective measure in respect of a match of the detected spectrum of the first generation with one of the comparative spectra.

15 Claims, 5 Drawing Sheets

(51) Int. Cl.
  *G01N 21/3586* (2014.01)
  *G01J 3/10* (2006.01)

(56) References Cited

U.S. PATENT DOCUMENTS

| | | | |
|---|---|---|---|
| 8,427,653 | B2 | 4/2013 | Hacker et al. |
| 8,526,002 | B2 | 9/2013 | DeFlores et al. |
| 8,571,254 | B2 | 10/2013 | Ogura |

OTHER PUBLICATIONS

Hoshina et al. "Noninvasive Mail Inspection System with Terahertz Radiation", Applied Spectroscopy, Bd. 63, Nr. 1, Jan. 1, 2009, pp. 81-86, XP055193749, ISSN: 0003-7028, DOI: 10.1366/000370209787169713.

Nuss, Martin "Chemistry is Right for T-Ray Imaging", IEEE Circuits and Devices Magazine, IEEE Service Center, Piscataway, NJ, US, Bd. 12, Nr. 2, März 1996, pp. 25-30, XP011083276, ISSN: 8755-3996.

METHOD OF SPECTROMETRY AND SPECTROMETER

RELATED APPLICATION DATA

This application claims priority under 35 U.S.C. §119 and/or §365 to German Patent Application No. 10 2014 101 302.6 filed Feb. 3, 2014, the entire contents is incorporated herein by reference.

TECHNICAL FIELD

The present invention concerns a method of spectrometry on a spatially extensive sample with generation of a measure in respect of matching of a detected spectrum of a first generation with a or a plurality of predetermined comparative spectra of chemical substances, which includes the steps: determining at least one location of the first generation on the sample, irradiating the sample with electromagnetic radiation with a plurality of frequencies or a frequency band from a frequency range of between 1 GHz and 30 THz at the given location of the first generation, frequency-resolved detection of a measure in respect of the intensity of the electromagnetic radiation irradiated on to the sample at the location of the first generation and transmitted by the sample or reflected by the sample as the spectrum of the first generation, and calculating a respective measure in respect of a match of the detected spectrum of the first generation with each of the comparative spectra.

The present invention also concerns a spectrometer which is so designed and adapted that it can carry out such a method.

BACKGROUND

In a frequency range of electromagnetic radiation of between 1 GHz and 30 THz, also referred as the terahertz frequency range or far infrared frequency or spectral range, many materials like for example paper, cardboard, ceramic and a series of plastic materials are transparent and can be transilluminated. That entails potential applications in particular for imaging systems in quality, packaging and security control as well as for monitoring chemical reactions.

In that respect the frequency of 1 THz corresponds to a wavelength of the electromagnetic wave of 300 µm and a photon energy of 4.14 meV or 33 wave numbers. The radiation is accordingly not ionizing and, unlike for example X-ray radiation, at the other end of the electromagnetic spectrum, does not fall foul of health reservations.

Systems which operate in the stated frequency range of the electromagnetic spectrum however are used not only for the purposes of imaging but also for identifying chemical substances, that is to say for spectrometry. More specifically it has been found that certain chemical substances, for example those which are security-relevant like weapons, explosives or drugs, have characteristic absorption bands in the stated frequency range. If a spectrum, that is to say a frequency-resolved measure in respect of the intensity of the electromagnetic radiation reflected by or transmitted through a chemical substance is successfully recorded in the stated frequency range then that spectrum can be compared to known reference spectra which for example are stored in a database and the substance can be identified.

If such spectrometric methods and spectrometers are used in application environments outside the laboratory then it is necessary for them to operate quickly and also to be operable on the part of non-expert personnel. In addition outside the laboratory effects due to packagings and maskings around the chemical substances which are actually to be detected represent a challenge.

SUMMARY

Therefore an object of the present invention is to provide a method of spectrometry on a spatially extensive sample but also a spectrometer which is suitable for same, which permit the generation of reliable measurement results. Another object of the present invention is to provide such a spectrometric method and a spectrometer which is suitable for same, which make it possible to detect relevant information on a spatially extensive sample in the shortest possible measurement time. Another object of the present invention is to provide a spectrometric method and a spectrometer for carrying out that method, which are simple to operate for the user and which provide a simple basis for decision, for example in terms of security or quality control.

At least one of the above-mentioned objects is attained by a method of spectrometry on a spatially extensive sample with generation of a measure in respect of a match of a detected spectrum of a first generation with a or a plurality of predetermined comparative spectra of chemical substances, which includes the steps: determining at least one location of the first generation on the sample, irradiating the sample with electromagnetic radiation with a plurality of frequencies or a frequency band from a frequency range of between 1 GHz and 30 THz at the given location of the first generation on the sample, frequency-resolved detection of a measure in respect of the intensity of the electromagnetic radiation irradiated on to the sample at the location of the first generation and transmitted by the sample or reflected by the sample as the spectrum of the first generation, and calculating a respective measure in respect of a match of the detected spectrum of the first generation with one of the comparative spectra wherein if the calculated measure in respect of the match of the detected spectrum of the first generation with one of the comparative spectra lies in a predetermined region a measure in respect of a match of at least one detected spectrum of a second generation with each of the comparative spectra is generated by performance of the following steps: determining a predetermined number of locations of the second generation so that all locations of the second generation on the sample are different from each other and from the location of the first generation and all locations of the second generation are arranged on the sample in a predetermined region around the location of the first generation, irradiating the sample with electromagnetic radiation with the plurality of frequencies or the frequency band from a frequency range of between 1 GHz and 30 THz at the locations of the second generation on the sample, frequency-resolved detection of a respective measure in respect of the intensity of the electromagnetic radiation irradiated on to the sample at the locations of the second generation and transmitted by the sample or reflected by the sample as spectra of the second generation, and calculating a respective measure in respect of a match of each spectrum of the second generation with each of the comparative spectra.

If a spectrometric measurement in the THz frequency range is performed at a location on a spatially extensive sample then the measured or detected spectrum is compared to a number of predetermined comparative spectra which each belong to a chemical substances. In that respect that comparison can produce substantially three results which are to be distinguished from each other: there is none of the chemical substances identified by the predetermined comparative spectra ("green"), there is a sufficient probability at that location that there is a chemical substance identified by one of the predetermined comparative spectra ("red") or a decision between the two above-mentioned scenarios is not clearly possible ("yellow"). To give the user in particular in the two last-mentioned scenarios a clear or better basis for decision for further actions the present invention describes a method as to how in the immediate vicinity of the location of the first measurement (first generation) further measurements (second and further generations) can be implemented in order to obtain the necessary spectrometric but also spatial information as quickly and reliably as possible.

A spatially extensive sample in the sense of the present invention is a three-dimensional article, in particular a pack, packet or an envelope of paper or cardboard, plastic or another material which is transparent to electromagnetic radiation in the THz frequency range.

Chemical substances which can be detected with an embodiment of the method according to the invention and/or of the spectrometer according to the invention are for example drugs like heroin, metamphetamine or ecstasy, explosives like PTN, RDX or SEMTEX-H, filling and extender agents like α-lactose, paracetamol or caffeine, biological or chemical weapons like anthrax or so-called stimulants like β-lactose, p-aminobenzoic acid (PABA), tartaric acid or maltose.

Accordingly in an embodiment a use of the present method according to the invention and the spectrometer according to the invention is the identification of drugs and explosive, in particular at the incoming mail checking office in public buildings or businesses.

In accordance with the present invention the term terahertz frequency range (THz frequency range) is used to mean a frequency range of between 1 GHz and 30 THz, preferably however a frequency range of between 100 GHz and 5 THz.

To be able to detect the characteristic (absorption) spectrum of a chemical substance it is necessary for the substance to be irradiated either with a plurality of mutually different frequencies or an entire frequency band from the stated frequency range. In that respect the frequency band can also embrace the entire frequency range.

In that respect in an embodiment the identical frequencies or the identical frequency band is used for all measurements at the individual locations on the sample.

To record the spectra it is necessary to detect in frequently-resolved fashion a measure in respect of the intensity of the electromagnetic radiation which is passed or irradiated on to the extensive sample and which is either transmitted through the sample or is reflected by the sample.

In that respect for frequency-resolved detection of a measure in respect of the intensity, the measure can be measured directly in frequency-resolved fashion. Alternatively it is possible to implement a measurement in the time domain as is the case in relation to the time-resolved THz spectrometers (TDS) which are also described hereinafter. In that respect the values measured in the time domain for the electrical field of the radiation are subsequently transferred into the frequency range by Fourier transform. This kind of frequency-resolved ascertainment of the measure in respect of intensity is also referred as detection in accordance with the present invention.

The term measure in respect of the intensity of the electromagnetic radiation is used in accordance with the present invention to denote in particular the intensity of the radiation itself, but also the electrical field of the radiation, the square of which is proportional to the intensity.

In an embodiment of the invention the detected spectra and the comparative spectra are extinction spectra, in respect of which the extinction of the electromagnetic radiation, due to the extensive sample or the chemical substances, is plotted in relation to frequency.

While initially it is immaterial for implementing the basic idea of the present invention whether the spectrum of the spatially extensive sample is detected in a reflection geometry or in a transmission geometry in an embodiment a transmission geometry in which the sample is disposed between a source for the electromagnetic radiation and a detector for the transmitted radiation is preferred. In transmission geometry the absorption lines of the chemical substances to be identified are more pronounced.

In an embodiment the given location on the sample, at which the spectrum is detected, is that location on the surface of the sample, at which the electromagnetic radiation passes into the sample and is transmitted from there through the sample or reflected by the sample.

The term comparative spectrum is used to denote a previously measured or calculated spectrum of a given chemical substance. That is stored for example in a database of the control and evaluation device of the spectrometer. A spectrum detected at a location on the sample is compared to that comparative spectrum.

Such a comparison between a detected spectrum and a comparative spectrum is effected in accordance with the present invention by calculation of a measure in respect of a match of the detected spectrum with the comparative spectrum.

Such a measure in respect of a match between the detected spectrum and the comparative spectrum is for example the mathematical cross-correlation between the two spectra. Such a measure in respect of the match can also be considered as a probability that the chemical substance detected by spectrometric measurement at the given location is or is not one of the chemical substances identified by one of the comparative spectra.

In accordance with the present invention those measurements at various locations which are either the cause of subsequent measurement at other locations (parents) or are the consequence of measurements with an inadequate result at other locations (descendants) are combined together to give a generation.

While in a simple example it is assumed that the first generation of spectra includes only a single spectrum at a single location on the sample the first generation can alternatively also involve a plurality of spectra detected at locations distributed over the sample.

In an embodiment the location or locations of the first generation on the sample is or are determined by a random selection or a selection of the location on the sample by a user.

In an alternative embodiment of the invention for determining a location or a plurality of locations of the first generation on the sample a user selects on the sample a region, within which a random selection of the location or locations then occurs. That is advantageous in particular when the user sees an image of the sample in the spectrometer and can establish the region in which the individual spectrometric measurements are to take place. An envelope can serve as an example in that respect, in which case the user advantageously selects the external contour of the envelope as that region, within which a random selection of the location or locations for the spectrum or spectra of the first generation then takes place.

If the measure in respect of a match of the detected spectrum of the first generation with one of the comparative spectra lies in a predetermined region then descendants for that spectrum of the first generation are generated by further measurements being implemented in the environment of the location of the spectrum of the first generation, in which case a respective measure in respect of a match of at least one detected spectrum of the second generation with each of the comparative spectra is generated.

In that case the decision threshold as to whether a further generation of spectra is or is not produced is predetermined for example by the user. An example of a test as to whether the calculated measure in respect of the match of the detected spectrum of the first generation with one of the comparative spectra lies in a predetermined region is for example the answer to the question of whether the probability that the detected spectrum identifies one of the chemical substances characterized by the comparative spectra is greater than 50%. In such a case for example after a single measurement in the first generation it is too early to set off an alarm or there is still not any adequate basis for decision at all. The detection of further spectra in the second generation is subsequently implemented.

In particular in an embodiment of the invention a measure in respect of a match of a spectrum with the n+1-th generation with each of the comparative spectra is generated only when a probability that at the location on the sample at which the spectrum of the n-th generation was detected, there is a chemical substance, with the comparative spectrum of which the detected spectrum was compared, is greater than a predetermined threshold value.

Thus firstly a predetermined number of locations of the second generation, which differ from each other but also from the location of the first generation, are determined in the environment, that is to say in a predetermined region, around the location of the first generation, at which the spectrometric measurements are then carried out.

To determine the locations of the second but also each subsequent generation, in an embodiment they can be so selected that each is arranged at a predetermined spacing and with a predetermined direction from the respective location of the preceding generation. Measurements in respect of the descendants are then effected in an established spatial pattern around the parent generation.

In an alternative embodiment the locations of the n+1-th generation (descendants) on the sample are determined with the following steps in the specified sequence: defining a region around the location of the n-th generation (parents), preferably a circle with a radius r, randomly selecting a number of locations in the defined region, wherein the number of locations randomly selected in said step is greater than the predetermined number of the locations to be determined of the n+1-th generation, determining a first location of the n+1-th generation from the amount of the locations selected in the preceding step, determining a further location of the n+1-th generation from the amount of the previously selected locations in the defined region, wherein that location is determined, which is at a maximum spacing from the location of the n-th generation and from all previously determined locations of all previous generations in the defined region, and repeating the preceding steps until the predetermined number of locations of the n+1-th generation is determined.

Such a selection of the locations at which the spectrometric measurements of the descendant generation is effected has the advantage that on average it permits a maximized information attainment over the sample in the shortest possible time.

In that respect in an embodiment of the invention the first generation of the n+1-th generation is randomly determined. In an alternative embodiment the first generation of the n+1-th generation like the further locations of the n+1-th generation is determined from the amount of the previously selected locations in the defined region as that location which involves a maximum spacing from the locations of all previous generations in the defined region.

In an embodiment of the invention in the operation of determining the locations on the sample for a new generation a gradient of spectra between at least two measures generated at two different locations in respect of a match of a detected spectrum with at least one of the comparative spectra, preferably all comparative spectra, are taken into consideration. Preferably however the gradients between all previously generated measures in respect of a match of a detected spectrum with one of the comparative spectra are taken into consideration. In that way it is possible to determine a direction in which the probability of the existence of a given chemical substance identified by a comparative spectrum increases and generate descendants in specifically targeted fashion in that direction.

It will be appreciated that the present invention is not limited to the production of two generations of spectra, but without limitation three or more generations can be produced or in an embodiment are produced as may be desired.

For that purpose in an embodiment of the invention when the calculated measure in respect of the match of a detected spectrum of the second or generally n-th generation at a location on the sample with one of the comparative spectra lies in a predetermined region a respective measure in respect of a match of a detected spectrum with a third or generally n+1-th generation with one of the comparative spectra is generated by performance of the following steps: determining a predetermined number of locations of the third or n+1-th generation so that all locations of the third or n+1-th generation on the sample are different from each other and from the locations of all other generations and all locations of the third or n+1-th generation are arranged on the sample in a predetermined region around the location of the second or n-th generation, irradiating the sample with electromagnetic radiation with the plurality of frequencies or the frequency band from a frequency range of between 1 GHz and 30 THz at the locations of the third or n+1-th generation on the sample, frequency-resolved detection of a respective measure in respect of the intensity of the electromagnetic radiation irradiated on to the sample at the locations of the third or n+1-th generation and transmitted by the sample or reflected by the sample as the spectra of the third or n+1-th generation, and calculating a respective measure in respect of a match of each detected spectrum of the third or n+1-th generation with each of the predetermined comparative spectra.

In that respect in an embodiment of the invention it can be appropriate if the maximum number of generations of detected spectra is limited to a predetermined value, for example 50.

It has also been found however that frequently limiting the maximum number of generations of detected spectra is not required if in embodiments other boundary conditions are imposed and thus the descendants "die out" sometime.

Such a boundary condition is the predetermined number of locations on the sample in a generation, at which in a generation of spectra same are detected. In an embodiment that predetermined number can be constant over the generations, with the increasing order of the generations it can decrease or it may embrace hybrid forms thereof.

In a specific embodiment spectra are detected at three locations in the second generation, in the third generation spectra are detected at two locations and in the fourth and each further generation only one respective spectrum is detected at a location.

In an embodiment of the invention such a rule for the number of descendants in a generation can be relaxed in that, if at a location in a generation there is no chemical substance specified by the comparative spectra with certainty (that is to say with a degree of probability which is above a predetermined threshold value), a further and preferably precisely one further descendant is produced in the same generation to maximize the attainment of information in that generation. For that purpose, in an embodiment, when for a spectrum of the n-th generation, that is detected at a location on the sample, there is no probability that there is at that location on the sample a chemical substance, with the comparative spectra of which the detected spectrum was compared, which is greater than a predetermined threshold value, a further measure is generated in the n-th generation in respect of a match of a detected spectrum at a further location with one or a plurality of predetermined comparative spectra of chemical substances.

To maximize the attainment of information by the production of an additional descendant in the same generation under the above-mentioned conditions a further embodiment of the invention provides that the further location of the n-th generation on the sample is determined with the following steps in the specified sequence: defining a region around the location of the n+1-th generation, preferably a circle with a radius r, and selecting a location in the defined region, in the environment of which there is a minimum density of locations at which spectra were detected, as the further location.

In a further embodiment of the invention when for a spectrum of the n-th generation, that is detected at a location on the sample, there is no probability that there is a chemical substance at that location on the sample, to the comparative spectrum of which the detected spectrum was compared, which is greater than a predetermined threshold value, the spectrum detected at that location is used as a reference spectrum for the other detected spectra or spectra still to be detected. For that purpose in an embodiment the reference spectrum is removed from the other detected spectra as an offset.

In an embodiment of the invention the locations on the sample, for which a spectrum was detected, are displayed in a schematic view on a display screen. In that respect in an embodiment it is desirable if the schematic view includes an imaging of the sample, for example a photograph or a preferably live video recording of the sample, on which the locations on the sample, for which a spectrum was detected, are graphically superimposed.

In an embodiment in each measurement at a location, that is to say the measure in respect of a match of a detected spectrum with at least one of the predetermined comparative spectra, is displayed in color-coded fashion at the corresponding location in the schematic view. In that way the user can quickly see the result of the measurements and this gives him a simple possible way of arriving at a decision.

Insofar as the present invention also concerns a spectrometer for spectrometry at a spatially extensive sample that is adapted to carry out the above-described spectrometry method and all its embodiments.

Insofar as hitherto aspects of the invention have been described in relation to the spectrometry method they also apply to the corresponding spectrometer. Insofar as the method is carried out with a spectrometer according to this invention it has the appropriate devices for that purpose. The spectrometer according to the invention has in particular a control device and an evaluation device which control the spectrometer and detect and evaluate the spectra so that the method according to the invention can be carried out.

While the spectrometer according to the invention can be implemented with any kind of source and detector which make it possible to simultaneously or successively pass various frequencies from the frequency range of between 1 GHz and 30 THz on to the multi-layer structure and to detect same, optoelectronic approaches are particularly suitable for coherent production and detection of the terahertz radiation for implementation of the spectrometer according to the invention.

In order to produce such an optoelectronic spectrometer having a source and a detector for the frequency range of between 1 GHz and 30 THz it has a laser, a first optoelectronic high-frequency component as the source and a second optoelectronic high-frequency component as the detector for the electromagnetic radiation, and a beam divider which is so set up and arranged that in operation of the spectrometer it passes a part of the electromagnetic radiation emitted by the laser on to the first high-frequency component and a part of the electromagnetic radiation emitted by the laser on to the second high-frequency component.

In an embodiment of such a spectrometer the laser is a laser for producing ultra-short electromagnetic pulses, preferably with a pulse duration of 150 fs or less.

The first and second optoelectronic high-frequency components as the source and detector respectively for the electromagnetic radiation in a frequency range of between 1 GHz and 30 THz, in an embodiment, is in each case alternatively a photoconductive switch or an electrooptical crystal. When using an electrooptical crystal the non-linear effects in the crystal are utilized to produce or detect from the electromagnetic radiation of the laser the electromagnetic radiation in the frequency range of between 1 GHz and 30 THz.

When using a photoconductive switch, optionally in combination with a respective antenna connected thereto, the impingement of a short electromagnetic pulse on the photoconductive switch causes a corresponding electrical biasing of the high-frequency component, a short current pulse in the component and thus the emission of a wide-band pulse in the terahertz frequency range. The short electromagnetic pulse of the laser on the detector side in comparison serves to temporarily switch the detector by means of the photoconductive switch and thus to render measurable the electrical field of the electromagnetic radiation in the THz frequency range, that simultaneously impinges on the high-frequency component of the detector. If a current is measured at the feed lines of the photoconductive switch of the high-frequency component used as the detector then the field of the electromagnetic terahertz radiation which is incident on the high-frequency component can be detected in time-resolved fashion.

The electrical field of the electromagnetic THz radiation impinging on the detector drives charge carriers in the longitudinal direction over the switch. In that case a current flow is possible only when the photoconductive switch is closed at the same time, that is to say the switch is irradiated with electromagnetic radiation from the laser. As the electromagnetic pulse used for switching the photoconductive switch is short in relation to the time configuration of the electrical field of the pulse received by the detector in the THz frequency range the electrical field of the THz signal can be measured or sampled in time-resolved fashion, by a time displacement between the THz pulse impinging on the switch and the electromagnetic pulse used for switching the photoconductive switch being introduced and varied during the measurement procedure.

The time-resolved electromagnetic field detected in that way can be converted into a corresponding frequency-resolved spectrum by Fourier transform.

It will be appreciated that in an embodiment with a photoconductive switch as the detector for the THz radiation the spectrometer has a suitable current or voltage amplifier which is connected to the detector for detecting the currents by way of the switch of the detector.

The optoelectronic spectrometer with the high-frequency components according to the invention however, as an alternative to a laser with short electromagnetic pulses, can also be operated with monochromatic laser radiation. For that purpose a laser or also two lasers which are coupled together provide two laser frequencies with a frequency difference equal to the electromagnetic radiation to be used for the spectrometry process, in the frequency range of between 1 GHz and 30 THz. They are spatially superimposed. The resulting electromagnetic beat signal is applied to the optoelectronic high-frequency components as the source and detector. The beat signal then here produces monochromatic electromagnetic radiation in the THz range.

In such an embodiment the frequency of the electromagnetic radiation in the THz range is set or tuned by attuning the differential frequency between the two electromagnetic radiation components generated by the laser or lasers.

BRIEF DESCRIPTION OF THE FIGURES

Further advantages, features and possible uses of the present invention will be apparent from the following description of a specific embodiment and the related Figures.

DETAILED DESCRIPTION OF PARTICULAR EMBODIMENTS

In the Figures identical components are denoted by the same references.

Figure 1:
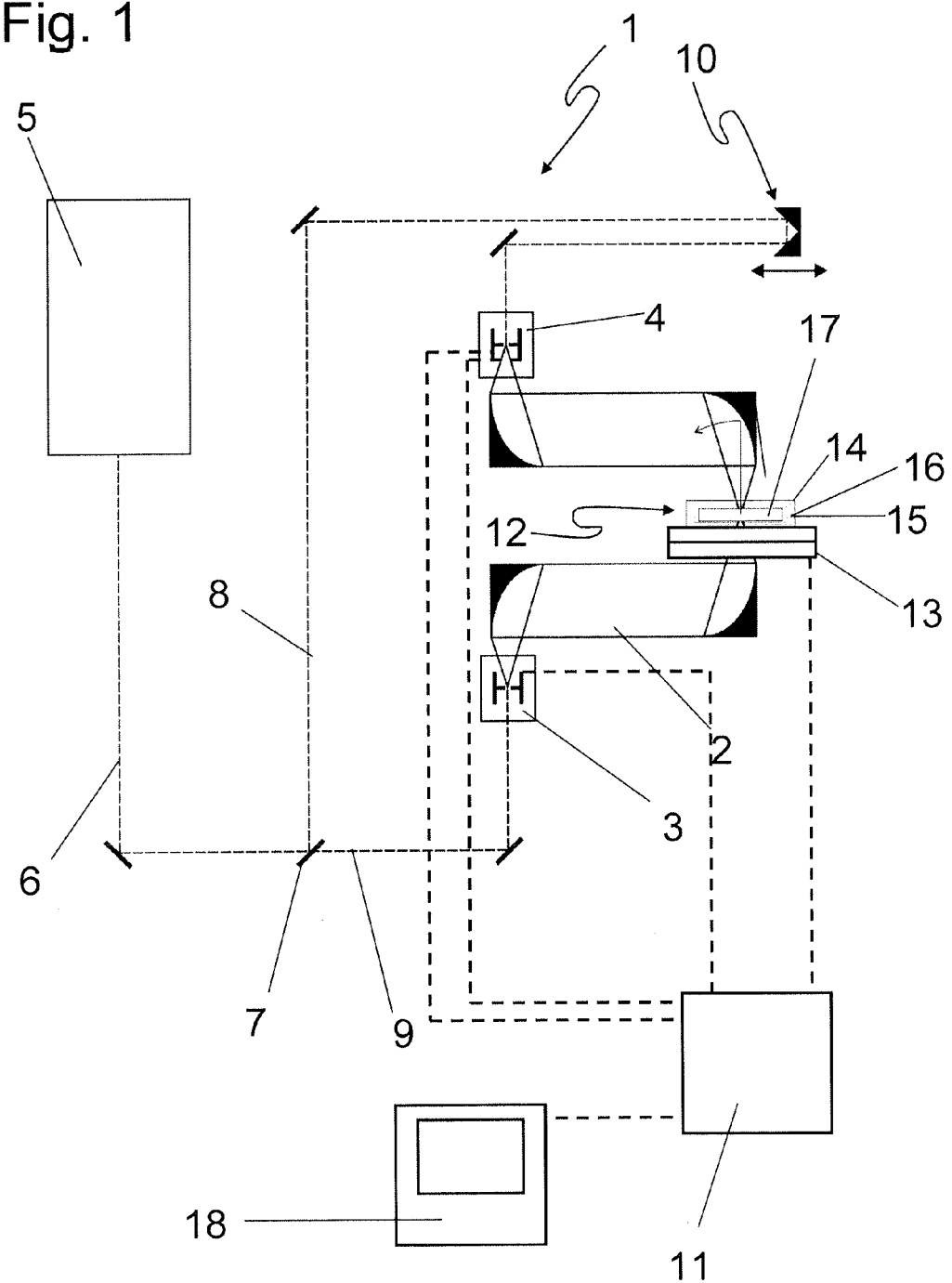
FIG. 1 shows a diagrammatic plan view of a spectrometer according to the present invention.

FIG. 1 diagrammatically shows the structure of a spectrometer 1 according to the invention, in which the electromagnetic high-frequency radiation 2 in a frequency range of between 1 GHz and 30 THz is produced and detected with photoconductive switches as a source 3 and a detector 4 for the high-frequency radiation.

The very heart of the illustrated spectrometer 1 is a laser 5 for producing short electromagnetic pulses 6 in the infrared spectral range. The pulse duration of the pulses produced by the laser 5 is about 100 fs. Each pulse 6 produced by the laser 5 is divided at a beam divider 7 into two spatially separated pulses 8, 9 of approximately equal power. In that case the travel lengths of the optical and high-frequency signals on the path from the beam divider 7 and the source 3 to the detector 4 on the one hand and from the beam divider 7 by way of a delay section 10 to the detector 4 on the other hand are so adapted that the high-frequency signal 2 impinges on the detector 4 simultaneously with the second part 8 of the pulse 6, the first part 9 of which caused the production of the high-frequency pulse 2 in the source 3.

In the illustrated embodiment the source 3 and the detector 4 each comprise a high-frequency component which is in the form of a photoconductive switch with a respective antenna for the high-frequency radiation 2.

Each of the high-frequency components 3, 4 has a dipole structure as its antenna. Each of the dipole antennas has in its center an interruption which, together with a photoconducting semiconductor substrate disposed under the antenna structure forms a photoconductive switch. The electromagnetic radiation produced by the laser 5 in the form of short pulses 6 is focused on to that photoconductive switch. In that respect it is also alternatively possible for the electromagnetic radiation produced by the laser 5 to be guided on to the photoconductive switch by means of optical light guide fibers. In such an embodiment it is possibly necessary to compensate for the dispersion which the individual pulses experience in the optical fiber.

Both the source 3 and also the detector 4 have two respective feed lines for the respective dipole antenna.

In the illustrated embodiment the semiconductor substrate for the photoconductive switch is a gallium arsenide grown at low temperatures, with short charge carrier lifetimes or charge carrier capture times.

In operation of the spectrometer a rectangularly modulated bias voltage is applied by way of the feed lines of the antenna to the high-frequency component used as the source 3. In that case the rectangular modulation serves to be able to detect the electromagnetic radiation at the detector side by means of a lock-in amplifier, the reference signal of which is phase-coupled to the modulation of the bias voltage of the source 3. Short-term closure of the photoconductive switch causes the production of a short current pulse by way of the antenna, which leads to the emission of a wide-band high-frequency pulse 2 by the antenna.

If the high-frequency component 4 used on the detector side is considered the current flowing by way of the antenna and the photoconductive switch formed thereby is there detected or measured. For that purpose the high-frequency component 4 is connected to a control and evaluation device 11. In the present case that is formed by a conventional industrial PC. The control and evaluation device 11 is also connected to a monitor 18 for showing the measurement results.

In that arrangement the electromagnetic field of the high-frequency pulse 2, that impinges on the antenna of the detector 4, leads to driving of charge carriers by way of the antenna or the switch and thus a current. It will be noted however that the current can flow by way of the antenna only at the moment when the photoconductive switch is closed by the reception of an electromagnetic pulse 8 of the laser 5. As the electromagnetic pulse used for closing the photoconductive switch on the detector side is short in time in relation to the high-frequency pulse impinging on the antenna the electrical field of the high-frequency pulse 2 can be sampled in time-resolved fashion by displacement of the arrival times of the two relative to each other by means of the delay section 10. That time-resolved electrical field of the electromagnetic high-frequency pulse 2 can be converted by means of a Fourier transform into an intensity spectrum in the frequency domain.

In the illustrated embodiment of the spectrometer in FIG. 1 the sample 12 is arranged on an x-y positioning table 13 which is driven by motor means and moved automatedly actuated by the evaluation and control device 11. By means of the positioning table 13 it is possible during the measurement procedure to adjust the location on the sample 12, at which the electromagnetic high-frequency radiation 2 is incident on the sample 12.

In this example the sample 12 is an envelope 17 in which SEMTEX-H 14 is contained, being again packaged in two paper packs 15, 16. In this case the sample 12 forms the extensive sample in accordance with the present invention and SEMTEX-H 14 is the chemical substance to be detected by spectrometer means.

Figure 2:
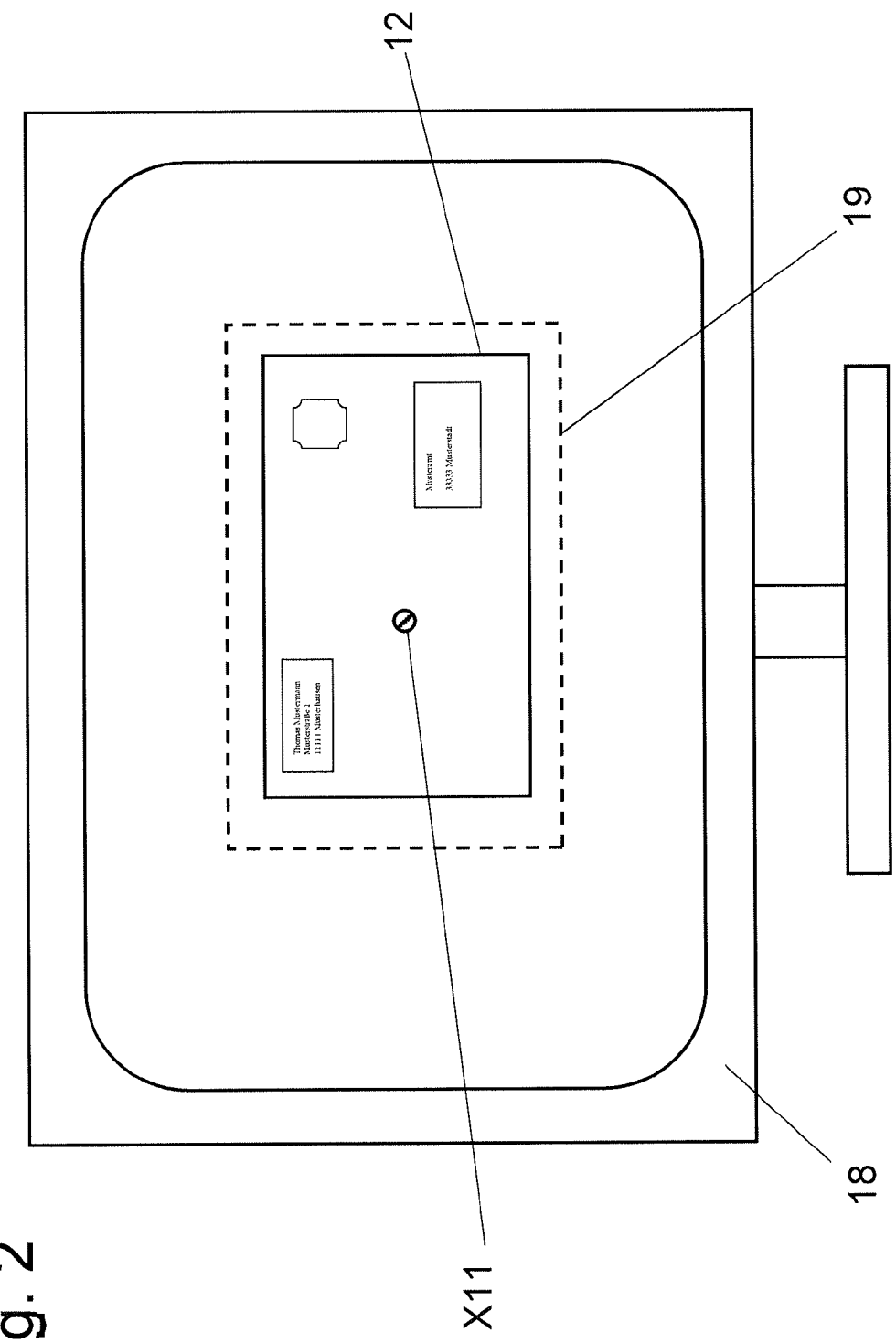
FIG. 2 shows a view of a measure in respect of matching of a detected spectrum of the first generation with a comparative spectrum on a display screen.

FIG. 2 now diagrammatically shows the display of the measurement results of the spectrometer 1 of FIG. 1 on the monitor 18. In that case FIG. 2 shows the view at the beginning of the measurement operations on an envelope 12, the content of which is to be tested for dangerous substances without opening it at the incoming mail station of a business. In that case the monitor 14 shows a digital photograph of the envelope 12, in the way it is disposed in the beam path of the spectrometer 1.

In a first step the user establishes by means of a mouse (not shown) a measuring area 19, within which all locations at which spectra are to be measured or detected must lie.

In the described embodiment the control and evaluation device 11 now randomly selects a location X11 within the measuring area 19, at which the spectrum of the first generation of spectra is detected. While here for the sake of simplicity it is assumed that there is only one spectrum at a single location X11 in the first generation of spectra a plurality of spectra in the first generation of spectra could equally well be detected at various locations on the sample.

In the example described here it is assumed that the spectrum detected at the location X11 exhibits a high correlation with a comparative spectrum stored in a database of the control and evaluation device 11 for SEMTEX-H. In that case the correlation is above a defined threshold value. The location X11 in the view on the monitor 14 is correspondingly marked in the color "red" (diagrammatically shown in the form of hatching). If an alarm for example were triggered on the basis of that single measurement by the user the risk of a false alarm would be markedly increased.

Figure 3:
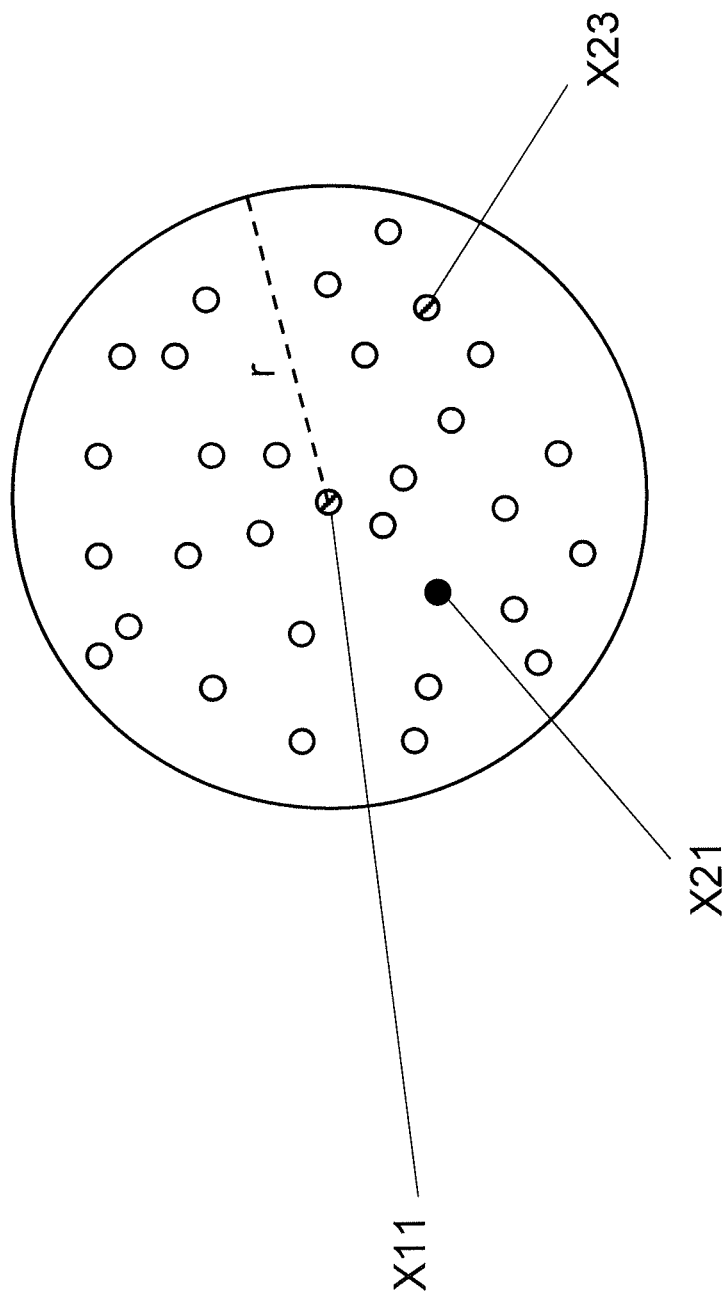
FIG. 3 shows an enlarged diagrammatic view of the generation of detected spectra of the second generation.

As the correlation between the spectrum detected at the location X11 and the comparative spectrum of SEMTEX-H is above the preset threshold value then in accordance with the invention spectra of a second generation are detected at further locations in the immediate area around the location X11. That procedure is diagrammatically shown in FIG. 3 showing an enlarged view around the point X11.

The evaluation software defines a surrounding region within a radius r around the location X11 in which all descendants of the second generation, that is to say spectra of the second generation, must lie. To determine the locations X2$n$ of the second generation of spectra random locations, in the present example 33 locations, are randomly selected within the circle of a radius r around the location X11. Those randomly selected locations are marked in FIGS. 3 and 4 in the form of empty circles, those auxiliary points not being displayed to the user. Once again randomly, one of those locations is selected as the first descendant X21. The further locations X2$n$ of the second generation are then so determined that they respectively involve a maximum spacing from all of the previously selected locations X11, X2$n$, for which a spectrum has already been detected or for which a spectrum is still to be detected. It is possible in that way to ensure that the locations of a generation are distributed around the location of the previous generation in such a way that a maximized production of information over the sample is achieved.

In the example described herein spectra at three locations X21, X22, X23 are detected in the second generation, spectra at two locations X31, X32 are detected in the third generation and a respective spectrum at a location X41, Xi1 is detected in the fourth and each further generation. In that case the maximum number of generations i in this example is additionally limited to 50.

Figure 4:
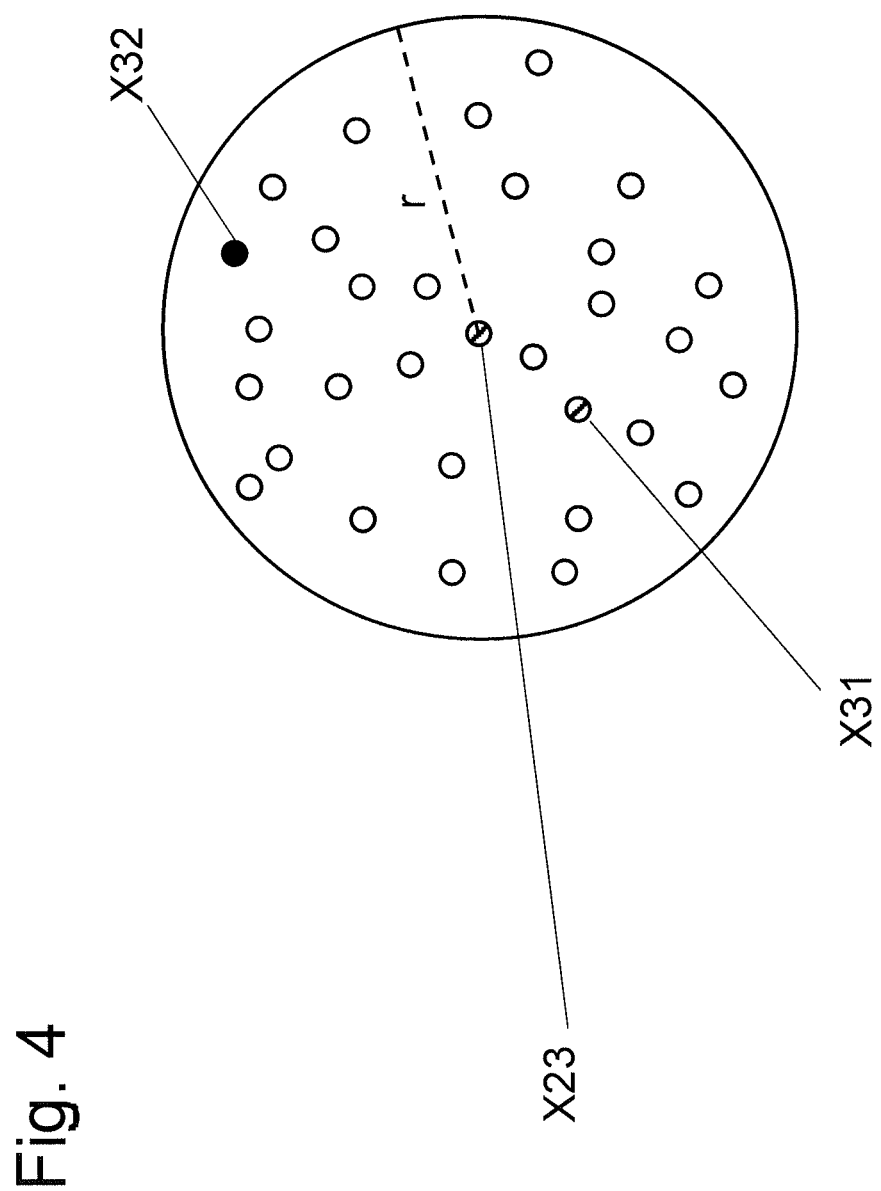
FIG. 4 shows an enlarged diagrammatic view of the generation of detected spectra of the third generation.

It is assumed that in the second generation a spectrum which has a sufficiently high level of correlation with the comparative spectrum of SEMTEX-H was detected only at the location X23. Consequently as shown in FIG. 4 a descendant in the third generation is subsequently generated only around the location X23. The necessary steps are repeated until the maximum permissible number of generations is reached or no further descendants are produced as the detected spectra at all locations no longer have a sufficiently high correlation with any one of the comparative spectra.

Figure 5:
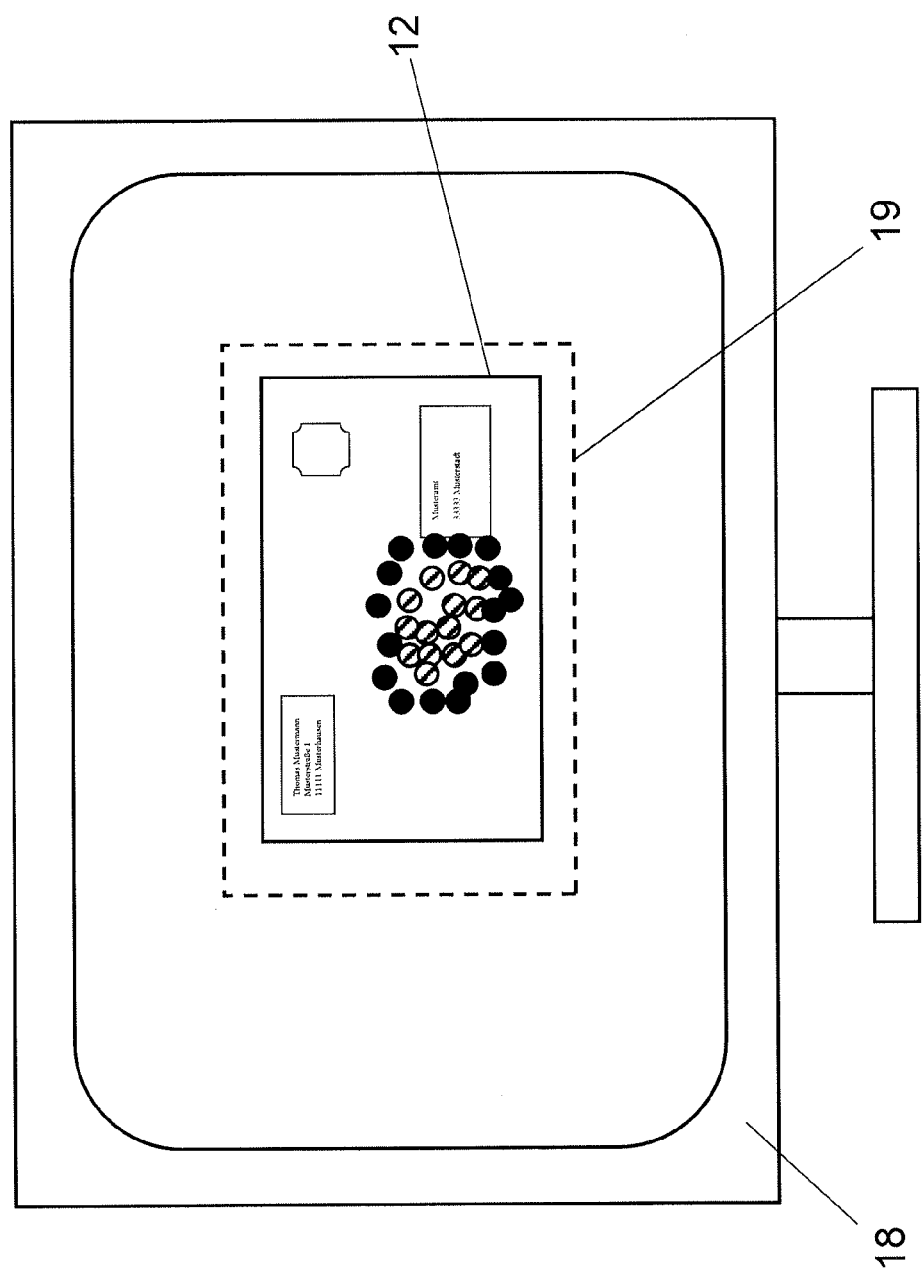
FIG. 5 shows one of a plurality of detected spectra of a plurality of generations on a display screen.

In realistic terms, for a hazardous substance located in an envelope, the procedure provides an image as is diagrammatically shown in FIG. 5, wherein information about the spatial distribution of the hazardous substance is also generated with comparatively few measurements.

For the purposes of the original disclosure it is pointed out that all features as can be seen by a man skilled in the art from the present description, the drawings and the claims, even if they are described in specific terms only in connection with certain other features, can be combined both individually and also in any combinations with others of the features or groups of features disclosed here insofar as that has not been expressly excluded or technical aspects make such combinations impossible or meaningless. A comprehensive explicit representation of all conceivable combinations of features is dispensed with here only for the sake of brevity and readability of the description.

While the invention has been described and illustrated in detail in the drawings and the preceding description that illustration and description is given only by way of example and is not deemed to be a limitation on the scope of protection as defined by the claims. The invention is not limited to the disclosed embodiments.

Modifications in the disclosed embodiments are apparent to the man skilled in the art from the drawings, the description and the accompanying claims. In the claims the word "have" does not exclude other elements or steps and the indefinite article "a" does not exclude a plurality. The mere fact that certain features are claimed in different claims does not exclude the combination thereof. References in the claims are not deemed to be a limitation on the scope of protection.

LIST OF REFERENCES 1 spectrometer
2 high-frequency radiation
3 source
4 detector
5 laser
6 electromagnetic pulse in the infrared spectral range
7 beam divider
8 second part of the pulse 6
9 first part of the pulse 6
10 delay section
11 control and evaluation device
12 sample
13 positioning table
14 SEMTEX-H
15, 16 paper packs
17 envelope
18 monitor
19 selection region X11 location of the spectrum of the first generation on the sample 12
X2n location of the spectra of the second generation on the sample 12
X3n location of the spectra of the third generation on the sample 12

The invention claimed is:

1. A method of spectrometry on a spatially extensive sample with generation of a measure in respect of a match of a detected spectrum of a first generation with a or a plurality of predetermined comparative spectra of chemical substances, which includes the steps:
 determining at least one location of the first generation on the sample,
 irradiating the sample with electromagnetic radiation with a plurality of frequencies or a frequency band from a frequency range of between 1 GHz and 30 THz at the given location of the first generation of a first order on the sample,
 frequency-resolved detection of a measure in respect of the intensity of the electromagnetic radiation irradiated on to the sample at the location of the first generation and transmitted by the sample or reflected by the sample as the spectrum of the first generation, and
 calculating a respective measure in respect of a match of the detected spectrum of the first generation with one of the comparative spectra,
 wherein if the calculated measure in respect of the match of the detected spectrum of the first generation with one of the comparative spectra lies in a predetermined region a measure in respect of a match of at least one detected spectrum of a second generation with each of the comparative spectra is generated by performance of the following steps:
 determining a predetermined number of locations of the second generation so that all locations of the second generation on the sample are different from each other and from the location of the first generation and all locations of the second generation are arranged on the sample in a predetermined region around the location of the first generation,
 irradiating the sample with electromagnetic radiation with the plurality of frequencies or the frequency band from a frequency range of between 1 GHz and 30 THz at the locations of the second generation on the sample,
 frequency-resolved detection of a respective measure in respect of the intensity of the electromagnetic radiation irradiated on to the sample at the locations of the second generation and transmitted by the sample or reflected by the sample as spectra of the second generation, and
 calculating a respective measure in respect of a match of each spectrum of the second generation with each of the comparative spectra.

2. The method as set forth in claim 1 wherein if the calculated measure in respect of the match of a detected spectrum of the second or n-th generation at a location on the sample with one of the comparative spectra lies in a predetermined region a respective measure in respect of a match of a detected spectrum with a third or n+1-th generation with one of the comparative spectra is generated by performance of the following steps:
 determining a predetermined number of locations of the third or n+1-th generation so that all locations of the third or n+1-th generation on the sample are different from each other and from the locations of all other generations and all locations of the third or n+1-th generation are arranged on the sample in a predetermined region around the location of the second or n-th generation,
 irradiating the sample with electromagnetic radiation with the plurality of frequencies or the frequency band from a frequency range of between 1 GHz and 30 THz at the locations of the third or n+1-th generation on the sample,
 frequency-resolved detection of a respective measure in respect of the intensity of the electromagnetic radiation irradiated on to the sample at the locations of the third or n+1-th generation and transmitted by the sample or reflected by the sample as spectra of the third or n+1-th generation, and
 calculating a respective measure in respect of a match of each detected spectrum of the third or n+1-th generation with each of the predetermined comparative spectra.

3. The method as set forth in claim 1 wherein the maximum number of generations of detected spectra is limited to a predetermined value.

4. The method as set forth in claim 1, wherein the predetermined number of locations on the sample, at which spectra are detected in a generation of spectra, is constant over the generations or decreases with increasing order of the generations.

5. The method as set forth in claim 1, wherein the locations of the n+1-th generation are so determined that each is arranged at a predetermined spacing and with a predetermined direction from the respective location of the n-th generation.

6. The method as set forth in claim 1, wherein the locations of the n+1-th generation on the sample are determined with the following steps in the specified sequence:
 defining a region around the location of the n-th generation, preferably a circle with a radius r,
 randomly selecting a number of locations in the defined region, wherein the number of locations randomly selected in said step is greater than the predetermined number of the locations to be determined of the n+1-th generation,
 determining a first location of the n+1-th generation from the amount of the locations selected in the preceding step,
 determining a further location of the n+1-th generation from the amount of the previously selected locations in the defined region, wherein that location is determined, which is at a maximum spacing from the location of the n-th generation and from all previously determined locations of all generations in the defined region, and
 repeating the preceding steps until the predetermined number of locations of the n+1-th generation is determined.

7. The method as set forth in claim 1, wherein when for a spectrum of the n-th generation, that is detected at a location on the sample, there is no probability that there is at that location on the sample a chemical substance, to the comparative spectra of which the detected spectrum was compared, which is greater than a predetermined threshold value, a further measure is generated in the n-th generation in respect of a match of a detected spectrum at a further location with one or a plurality of predetermined comparative spectra of chemical substances.

8. The method as set forth in claim 7 wherein the further location of the n-th generation on the sample is determined with the following steps in the specified sequence:
 defining a region around the location of the n−1-th generation, preferably a circle with a radius r, and selecting a location in the defined region, in the environment of which there is a minimum density of locations at which spectra were detected, as the further location.

9. The method as set forth in claim 1, wherein when for a spectrum of the n-th generation, that is detected at a location on the sample, there is no probability that there is a chemical substance at that location on the sample, to the comparative spectrum of which the detected spectrum was compared, which is greater than a predetermined threshold value, the spectrum detected at that location is used as a reference spectrum for the other detected spectra or spectra still to be detected and is preferably removed from the other detected spectra as an offset.

10. The method as set forth in claim 1, wherein in the operation of determining the locations on the sample for a generation a gradient between at least two measures generated at two different locations in respect of a match of a detected spectrum with at least one of the comparative spectra, preferably all comparative spectra, are taken into consideration.

11. The method as set forth in claim 1, wherein for determining a location or a plurality of locations of the first generation on the sample a user selects a region on or around the sample, within which a random selection of the location or locations is implemented.

12. The method as set forth in claim 1, wherein the locations on the sample, for which a spectrum was detected, are displayed in a schematic view on a display screen.

13. The method as set forth in claim 12 wherein the schematic view includes an imaging of the sample on which the locations on the sample, for which a spectrum was detected, are graphically superimposed.

14. The method as set forth in claim 12 wherein the measure in respect of a match of a detected spectrum with at least one predetermined comparative spectrum is displayed in color-coded fashion at the location in the schematic view.

15. A spectrometer for spectrometry at an extensive sample comprising
    a source for electromagnetic radiation with a plurality of frequencies or a frequency band from a frequency range of between 1 GHz and 30 THz,
    a detector for frequency-resolved detection of a measure in respect of the intensity of the electromagnetic radiation which is passed at an angle of incidence on to the multi-layer structure and which is transmitted by the multi-layer structure or reflected by the multi-layer structure, as a spectrum,
    a control device, and
    an evaluation device,
wherein the spectrometer is adapted to carry out a method as set forth in claim 1.

* * * * *